United States Patent
Murata et al.

(10) Patent No.: US 6,313,341 B1
(45) Date of Patent: Nov. 6, 2001

(54) PROCESS FOR THE PREPARATION OF PROSTAGLANDINS

(75) Inventors: Noriaki Murata; Atsunori Aramata; Tadashi Takeuchi, all of Takaoka (JP)

(73) Assignee: Fuji Yakuhin Kogyo Kabushiki Kaisha, Toyama (JP)

( * ) Notice: Subject to any disclaimer, the term of this patent is extended or adjusted under 35 U.S.C. 154(b) by 0 days.

(21) Appl. No.: 09/308,185

(22) PCT Filed: Nov. 14, 1997

(86) PCT No.: PCT/JP97/04158

§ 371 Date: May 14, 1999

§ 102(e) Date: May 14, 1999

(87) PCT Pub. No.: WO98/21179

PCT Pub. Date: May 22, 1998

(30) Foreign Application Priority Data

Nov. 14, 1996 (JP) .................................... 8-337396

(51) Int. Cl.$^7$ .................................. C07C 405/00
(52) U.S. Cl. ............................ 560/121; 562/503
(58) Field of Search .............. 560/121; 562/503

(56) References Cited

U.S. PATENT DOCUMENTS

| | | |
|---|---|---|
| 4,087,447 | 5/1978 | Collins et al. . |
| 4,543,421 | 9/1985 | Corey et al. . |
| 4,777,275 | 10/1988 | Campbell et al. . |
| 5,075,478 | 12/1991 | Behling et al. . |
| 5,329,035 | 7/1994 | Noyori et al. . |

FOREIGN PATENT DOCUMENTS

| | | |
|---|---|---|
| 0294757 | 12/1988 | (EP) . |
| 53108929 | 9/1978 | (JP) . |
| 6187638 | 5/1986 | (JP) . |
| 6344743 | 9/1988 | (JP) . |
| 63316786 | 12/1988 | (JP) . |
| 2255654 | 10/1990 | (JP) . |
| 692930 | 4/1994 | (JP) . |

OTHER PUBLICATIONS

Tetrahedron Letters, vol. 30, No. 1, pp 27–30, 1989.
J. Org. Chem. 1981, 46, 5221–5222.
J. Am. Chem. Soc., 112, pp7440–7441, 1990.
Collins et al., Chemical Reviews, vol. 93, No. 4 (1993) pp. 1533–1564.

*Primary Examiner*—Robert Gerstl
(74) *Attorney, Agent, or Firm*—Kolasch & Birch, LLP

(57) ABSTRACT

A hydroxy-1-alkyne is reacted with a tin hydride compound, and the obtained (E,Z)-hydroxyvinylstannanes are separated to give the (E)-substance which is further converted to a vinylcopper complex shown by

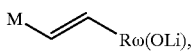

followed by the conjugate addition reaction with an α,β-unsaturated cyclopentenone, and the deprotecting reaction is subsequently carried out to prepare a prostaglandin or an intermediate of prostaglandins easily, efficiently and industrially favorably.

9 Claims, No Drawings

PROCESS FOR THE PREPARATION OF PROSTAGLANDINS

This application is the national phase under 35 U.S.C. §371 of PCT International Application No. PCT/JP97/04158 which has an International filing date of Nov. 14, 1997, which designated the United States of America.

TECHNICAL FIELD

The invention relates to a process for preparing prostaglandins having a broad physiological activity and intermediates thereof, easily, efficiently and industrially favorably.

BACKGROUND ART

Natural prostaglandins have a unique structure and are known as compounds showing a broad physiological activity in a small amount, attracting interest of many organic synthetic chemists, and it is desired to purely synthesize natural prostaglandins in which there is a difficulty for naturally obtaining them in a large amount in order to further study a minute biological activity, and furthermore a lot of synthetic work has been done from such reasons that a lot of structural analogues from natural prostaglandins can be synthesized and these prostaglandin analogues are interesting from the aspect of a drug development.

As one of the representative preparation processes of prostaglandins there is the process in which the omega side chain is introduced by affecting an organometallic reagent to an α, β-unsaturated cyclopentenone. Especially is well known such a process that a vinylstannane compound having an aimed omega side chain structure or its corresponding vinyliodide compound are converted to the vinylcopper complex to carry out the conjugate addition to the α, β-unsaturated cyclopentenone [U.S. Pat. No. 4,777,275 (JP, A, S63-316786), U.S. Pat. No. 4,543,421 (JP, B, S63-44743)]. Typically, a vinylstannane compound is prepared by affecting tin hydride under a radical condition after the addition of an acid unstable protective group such as a trialkylsilyl group to a free hydroxyl group which a terminal alkyne of a starting material has [U.S. Pat. No. 4,087,447 (JP, A, S53-108929)]. The conversion to the vinyliodide is done by treating the vinylstannane compound with iodine. An alkylmetal reagent is reacted with the obtained vinylstannane compound or its corresponding vinyliodide compound to give a vinylmetal compound, and subsequently a cuprous (I) salt is added to give a vinylcopper complex. Thereto is added an α, β-unsaturated cyclopentenone to give the 1,4-conjugate addition product. Since one more step is necessary to obtain a vinyliodide compound from a vinylstannane compound and there is no difference between the vinylstannane compound and the vinyliodide compound, there is no special advantage to derivatize it into the vinyliodide compound. Therefore, a vinylmetal compound via a vinylstannane compound is advantageous, though there is an unfavorable problem that a geometrical isomer accompanies in case of preparing the vinylstannane compound by the above process.

DISCLOSURE OF THE INVENTION

There are characteristics that natural type prostaglandins and many prostaglandin analogues have a double bond at 13, 14 positions and its geometrical configuration is (E)-configuration, though (E)-vinylstannane compound having an aimed omega side chain structure is necessary to construct this characteristic geometry. In the conventional preparation process of a vinylstannane compound, that is, the process of reacting a tin hydride compound with hydroxy-1-alkynes after protecting the hydroxy group thereof, (Z)-vinylstannane compound which is the geometrical isomer, is accompanied in ca. 20% (U.S. Pat. No. 4,543,421 (JP, B, S63-44743), and furthermore, the separation of the obtained (E)-and (Z)-vinylstannane compounds is extremely difficult even by the separation procedures by silica gel chromatography or rectification. Therefore, in the conventional process, it is used by the isolation even in an extremely low yield or the mixture of the geometrical isomers is used "in situ". In the latter case an undesirable geometrical isomer is inevitably coexisting in conjugate addition products after the reaction, and furthermore, the separation of the obtained (13E)-product and its geometrical isomer, (13Z)-product, by silica gel chromatography is extremely difficult, resulting in a low yield.

Further, the introduction of a protecting group to hydroxy-1-alkynes influences the yield of the deprotecting step to give prostaglandins finally. For the deprotecting reagent, an aqueous acid solution is used, though due to the instability of prostaglandins to acid, the reaction condition to use less amount of acid is favorable.

As a process to solve the geometrical problem, a selective process for the (E)-substance synthesis, which uses a zirconium compound, has been developed (B. H. Lipshutz et al., J. Am. Chem. Soc., 112, 7440, 1990). Namely, the (E)-alkenylziruconium intermediate was produced by the terminal alkyne compound constituting the omega side chain and the zirconocene reagent, and reacted with alkyllithium and the copper reagent to give the cuprate intermediate with which the α, β-unsaturated cyclopentenone was reacted to synthesize the prostaglandin intermediate. However, the zirconocene reagent is expensive, and also difficult to obtain in a large amount. Further, the production step of the terminal alkyne compound also includes a protection step for the hydroxyl group, which is also unfavorable for industrially producing prostaglandins.

As a process to solve the problem of the geometrical isomer without protection of the hydroxyl group in an omega side chain compound, there is a process developed by J. R. Behling et al., starting from (E)-bis(tributylstannyl) ethylene (Tetrahedron Letters, 30, 27, 1989, U.S. Pat. No. 5,075,478). This preparation process carries out the synthesis of the prostaglandin intermediate, wherein lithium 2-thienylcyanocuprate separately prepared is reacted with (E)-bis(tributylstannyl)ethylene to give vinylstannanylcuprate, reacted with epoxides, aldehydes or ketones to give "in situ" alkoxyvinylstannanes corresponding to an omega side chain, further added with the alkyllithium reagent to give the vinyllithium complex, here at added with the organocopper reagent separately prepared, followed by the reaction with the α, β-unsaturated cyclopentenone. By this method one pot synthesis of the prostaglandin intermediate can be attained, though the starting (E)-bis(tributylstannyl)ethylene must be produced via 2 steps described in the following. Namely, the process is that acetylene is converted to lithium acetylide, subsequently reacted with tributyltin chloride to give tributylethynylstannane with which tributyltin hydride is reacted to give (E)-bis(tributylstannyl)ethylene (J. Org. Chem., 46, 5221, 1981). A series of reaction procedures in the preparation process of the prostaglandin intermediate are fairly complex and the stable preparation with reproducibility starting from the above (E)-bis(tributylstannyl)ethylene can not expected even with a considerable technique. Further, the yield is a level of 30–68% and is not satisfactory. Thus it can not be said that this process is a favorably industrial process.

Therefore, the problem to be solved by the invention is to provide a process preparing prostaglandins and intermediates thereof, simply, efficiently and industrially advantageously.

As the result of making an extensive research to overcome these problems, the inventors found the process by which prostaglandins are prepared industrially advantageously by the process shown in the synthetic route (I).

Namely, hydroxy-1-alkyne shown by the formula (II) is reacted with the tin hydride to give (E,Z)-hydroxyvinylstannanes of the formula (IV) which are subsequently separated by silica gel chromatography to give the (E)-hydroxyvinylstannane of the formula (V). Subsequently, the tin part of the (E)-hydroxyvinylstannane and hydrogen of the hydroxyl group are respectively converted to the reactive copper part and lithium to give a vinylcopper complex of the formula (VI), followed by the 1,4-conjugate addition reaction with an α, β-unsaturated cyclopentenone of the formula (VII) to give a prostaglandin intermediate of the formula (VIII) It is aprocess for preparing a prostaglandin of the formula (I) finally via the deprotection process with acid.

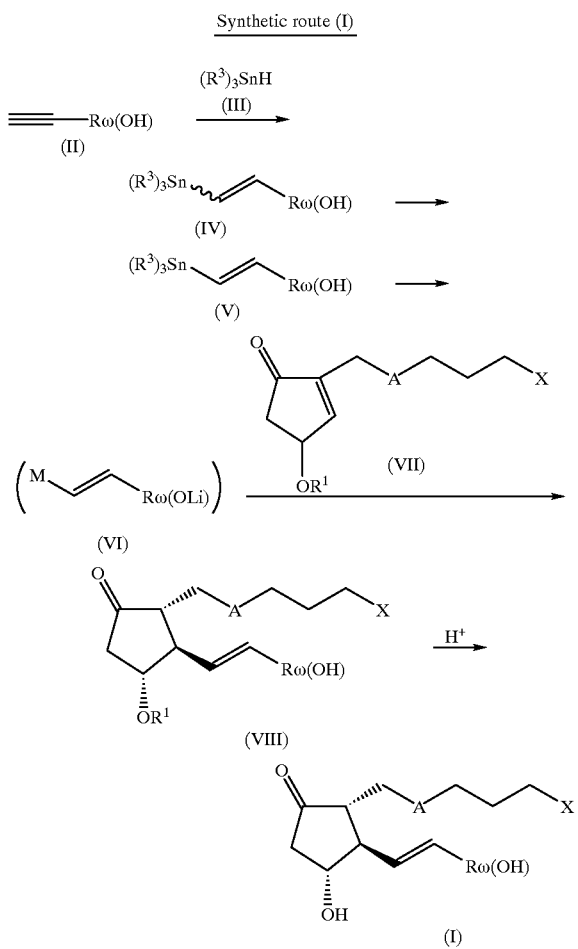

Synthetic route (I)

In the preparation process of prostaglandins by the above synthesis route are cited the following characteristics.

1) The hydroxy-1-alkyne shown by the formula (II) which is a starting material of the omega side chain can be converted to the hydroxyvinylstannanes shown by the formula (IV) even though hydroxy group is not protected.

2) Since in the stannanes shown by the formula (IV) contrasting to a tin compound added with a protective group the (E)-substance and the (Z)-substance can efficiently be separated by a chromatography method, the desired hydroxyvinylstannane of the formula (V) having (E)-configuration can be obtained in a good yield.

3) By converting the (E)-hydroxyvinylstannane to the vinylcopper complex shown by the formula (VI) and the subsequent 1,4-conjugate addition reaction with the α, β-unsaturated cyclopentenone of the formula (VII), the prostaglandin intermediate represented by the formula (VIII) is obtained in a high yield. In this case, as for an alkyllithium reagent among reagents added to convert the hydroxyvinylstannane represented by the formula (V) to the vinylcopper complex represented by the formula (VI) is added the total amount including a necessary amount for making the tin part into the reactive copper part and at least an equivalent amount corresponding to the tin compound for the metal exchange of hydrogen of the free hydroxyl group. The part in which hydrogen of the free hydroxyl group is exchanged by lithium does not react with the α, β-unsaturated cyclopentenone of the formula (VII), and easily returns to the hydroxyl group at a work-up stage. Accordingly, a starting material for the omega side chain having a free hydroxyl group is used to let the conjugate addition proceed in a good yield under the condition of adding excessively at least equivalent amount of alkyllithium to the tin compound at the stage of the copper complex formation.

4) By the treatment of the prostaglandin intermediate shown by the formula (VIII) with acid, the deprotection of the 11-positioned hydroxyl group proceeds easily. Prostaglandins are obtained in such a higher yield compared with the case that a protecting group of the hydroxyl group is present in the 11 position and the omega side chain.

According to the invention, prostaglandins and intermediates thereof could be prepared simply, efficiently and industrially advantageously.

MODE FOR CARRYING OUT THE INVENTION

The process for preparing prostaglandins according to the invention shown by the formula (I)

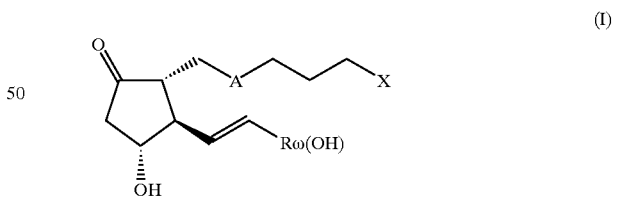

(wherein A is ethylene or (Z)-vinylene, X is $CH_2OR^2$ or $CO_2R^2$, $R^2$ is an alkyl group of the carbon number of 1–5, H or a protecting group, Rω(OH) is a straight chain or branched chain alkyl group of the carbon number of 4–10 having a secondary or tertiary hydroxyl group, the steric configuration of hydroxyl group is R, S or a mixture of R and S, the steric configuration of branched chain alkyl group is R, S or a mixture of R and S. Further, the stereochemistry of the formula (I) represents a relative steric configuration, and does not restrict an optically active substance or a racemic substance.) is as follows.

A hydroxy-1-alkyne shown by the formula (II)

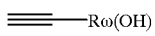
(II)

(Rω(OH) has a same meaning as described above) whose hydroxyl group is not protected, is reacted with a tin hydride shown by the formula (III)

$(R^3)_3SnH$ (III)

(wherein $R^3$ is a lower alkyl group of the carbon number of 1–6, phenyl or cyclohexyl) to prepare (E,Z)-hydroxyvinylstannanes shown by the formula (IV)

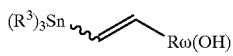
(IV)

($R^3$ and Rω(OH) have a same meaning as described above), and the separation of the (E)-substance and the (Z)-substance is carried out by column chromatography to prepare an (E)-hydroxyvinylstannane shown by the formula (V)

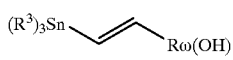
(V)

(wherein $R^3$ and Rω(OH) have a same meaning as described above).

As the hydroxy-1-alkyne (II) used in the reaction is favorably cited a 4-hydroxy-4-alkyl-1-alkyne shown by the formula (XIII)

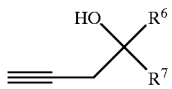
(XIII)

(wherein $R^6$ and $R^7$ are each independently a straight chain or branched chain alkyl group of the carbon number of 1–7 or hydrogen, and the steric configuration of the hydroxy group is R, S or a mixture of R and S) or a 3-hydroxy-1-alkyne shown by the formula (XIV)

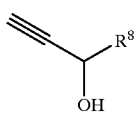
(XIV)

(wherein $R^8$ represents a straight chain or branched chain alkyl group of the carbon number of 3–9, and the steric configuration of the hydroxy group is R, S or a mixture of R and S).

More specifically are cited 4-hydroxy-4-methyl-1-octyne, 4-hydroxy-4,6-dimethylhept-5-ene-1-yne, 4-hydroxy-4,8-dimethylnon-7-ene-1-yne, 4-vinyl-4-hydroxy-1-octyne, 6-ethyloxy-4-hydroxy-4,5,5-trimethyl-1-hexyne, 4-hydroxy-4,7-dimethyldeca-5,7-diene-1-yne and the like. More preferably are cited 4-hydroxy-4-methyl-1-octyne, 4-hydroxy-4,6-dimethylhept-5-ene-1-yne which can be represented by the general formula (XIII), or 3-hydroxy-1-octyne, 4,4-dimethyl-3-hydroxy-1-octyne, 3-hydroxy-5-methyl-1-nonyne and the like which can be represented by the general formula (XIV). As the tin hydrides of the formula (III) used in the reaction can be cited compounds in which $R^3$ in the formula are a methyl, ethyl, propyl, butyl, pentyl, hexyl, phenyl and cyclohexyl groups and the like, and said compounds are used in 1–10 equivalent mole, preferably in 1–1.5 equivalent mole to hydroxy-1-alkynes, the starting materials. The reaction temperature in the reaction is 0–200° C., preferably 50–150° C., and it is reacted for about 1–12 hours. In the reaction, any special reagent is not added except the tin hydrides, though the reaction can also be carried out under the presence of a free radical initiator such as azobisisobutyronitrile or ultraviolet ray, giving the similar results. In the reaction an organic solvent is not specially necessary. Further, a special work-up is not necessary, and a reaction mixture is cooled to room temperature, followed by the silica gel column chromatographic separation of an (E)-substance and a (Z)-substance to give the (E)-substance. The production ratio of E/Z in the reaction is about 85:15. Hereupon, in vinylstannanes in which the hydroxyl group is protected by an acid-labile protecting group or the like, the chromatographic separation of the (E)-substance and the (Z)-substance is very difficult, though owing to the polarity difference by the free hydroxyl group the chromatographic separation can be possible.

In an ether such as tetrahydrofuran or diethyl ether, or an alkane such as pentane or hexane, or a mixed solvent of an ether or an alkane, a copper (I) salt shown by CuY (Y is —CN, —SCN or —$OSO_2CF_3$) and an alkyllithium reagent shown by $R^4Li$ ($R^4$ is a lower alkyl) are added to an (E)-hydroxyvinylstannane, or CuY (Y has a same meaning as described before), $R^4Li$ ($R^4$ has a same meaning as described before) and Lewis acid are added, or CuY (Y has a same meaning as described before), $R^4Li$ ($R^4$ has a same meaning as described before), Lewis acid and a lithium salt shown by LiZ (Z is a halogen atom which may be a fluorine, chlorine, bromine or iodine atoms, or —$OSO_2CF_3$) are added, giving a vinylcopper complex shown by the formula (VI)

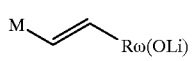
(VI)

(wherein M is a reactive copper part having Y and Li, or a reactive copper part having Y, Li and Lewis acid, or a reactive copper part having Y, Li, Lewis acid and LiZ, Rω(OLi) represents a group in which hydrogen of the hydroxyl group in Rω(OH) is exchanged by Li).

The amount of an alkyllithium reagent used in the invention requires the equivalent number to form the reactive copper part and at least the equivalent for metal-exchange of the hydroxyl group in a starting tin compound. According to this, the tin part of the tin compound is transformed to a reactive copper part, and hydrogen of the hydroxyl to lithium respectively. The M part which is the reactive copper part of the formula (VI) depends on a kind of reagents and an equivalent number of reagents. More particularly, the vinylcopper complex can be prepared, wherein the M part of the formula (VI) is shown by the formula (IX)–(XII)

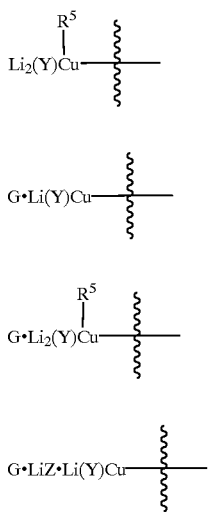

(IX)

(X)

(XI)

(XII)

(wherein $R^5$ represents $R^4$ or

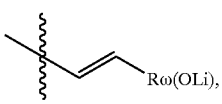

G represents Lewis acid, and $R^4$, Y, Z and Rω(OLi) have a same meaning before).

Under the condition that stochiometrically 1 equivalent of a copper (I) salt shown by CuY (Y has a same meaning as described before) and 3 equivalents of an alkyllithium reagent shown by $R^4$Li ($R^4$ has a same meaning as described before) against the hydroxyvinylstannane are added, a vinylcopper complex is formed in which $R^5$ of the reactive copper part shown by the formula (IX) is $R^4$ ($R^4$ has a same meaning as described before). Under the condition that stochiometrically 1 equivalent of CuY (Y has a same meaning as described before) and 4 equivalents of $R^4$Li ($R^4$ has a same meaning as described before) against the hydroxyvinylstannane are added, a vinylcopper complex is formed in which $R^5$ of the reactive copper part is as follows.

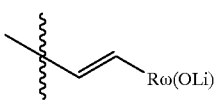

Under the condition that stochiometrically 1 equivalent of CuY (Y has a same meaning as described before), 2 equivalents of $R^4$Li ($R^4$ has a same meaning as described before) and 1 equivalent of Lewis acid against the hydroxyvinylstannane are added, a vinylcopper complex is formed in which the reactive copper part is shown by the formula (X). Under the condition that stochiometrically 1 equivalent of CuY (Y has a same meaning as described before) 3 equivalents of $R^4$Li ($R^4$ has a same meaning as described before) and 1 equivalent of Lewis acid against the hydroxyvinylstannane are added, a vinylcopper complex is formed in which $R^5$ of the reactive copper part shown by the formula (XI) is $R^4$ ($R^4$ has a same meaning as described before).

Under the condition that stochiometrically 1 equivalent of CuY (Y has a same meaning as described before), 4 equivalents of $R^4$Li ($R^4$ has a same meaning as described before) and 1 equivalent of Lewis acid against the hydroxyvinylstannane are added, a vinylcopper complex is formed in which $R^5$ of the reactive copper part is as follows.

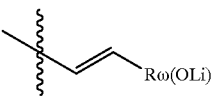

Under the condition that stochiometrically 1 equivalent of CuY (Y has a same meaning as described before), 2 equivalents of $R^4$Li ($R^4$ has a same meaning as described before), 1 equivalent of Lewis acid and 1 equivalent of lithium salt shown by LiZ (Z has a same meaning as described before) against the hydroxyvinylstannane are added, a vinylcopper complex is formed in which the reactive copper part is shown by the formula (XII) The addition sequence of the hydroxyvinylstannane, CuY (Y has a same meaning as described before), $R^4$Li ($R^4$ has a same meaning as described before) and LiZ (Z has a same meaning as described before) is not restricted, and even if the addition sequence of these reagents is changed, the aimed vinylcopper complex is formed, and there is no effect on the yield of the addition reaction.

The reaction temperature for preparing these vinylcopper complexes is −100–40° C., preferably −80–30° C. The reaction time is different depending on the reaction amount, the type of a used reagent, the type of a used solvent and the reaction temperature, though, usually from 1 min. to 8 hours.

As an alkyllithium reagent used in the invention are used methyllithium, buthyllithium or the like. As a Lewis acid reagent used in the invention are used boron trifluoride diethyl ether complex, trimethylsilyl chloride, aluminum chloride or the like. The conjugate addition reaction of a vinylcopper complex having a reactive part shown by the formula (IX)–(XII) and an α, β-unsaturated cyclopentenone of the formula (VII)

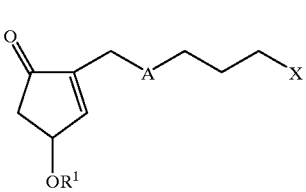

(VII)

(wherein $R^1$ is an acid labile protecting group such as tri($C_1$–$C_7$) hydrocarbonsilyl, tetrahydopyranyl, tetrahydrofuranyl, or the like, A and X have a same meaning as described before, and the formula (VII) does not restricts an optically active form or a racemic form) is carried out to produce an intermediate of prostaglandins shown by the formula (VIII)

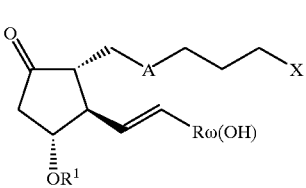

(VIII)

($R^1$, A, X and Rω(OH) have a same meaning as described before, and the stereochemistry of the formula (VIII) represents a relative steric configuration, and does not restricts an optically active form or a racemic form). In this reaction, the M part (M is shown by the formula (IX)–(XII)) of the vinylcopper complex is reacted with the α, β-unsaturated cyclopentenone, and the part (—OLi) in which hydrogen of the hydroxyl group is exchanged by lithium does not react and easily reverts to the hydroxyl group after a work-up stage.

As the α, β-unsaturated cyclopentenone shown by the formula (VII), X in the formula is $CH_2OR^2$ or $CO_2R^2$, and $R^2$ is an alkyl group of the carbon number of 1–5, H or a protecting group, and illustrative of alkyl groups of the carbon number of 1–5 are, for example, methyl, ethyl, propyl, butyl, pentyl and the like, and illustrative of protecting groups are a tri($C_1$–$C_7$) hydrocarbonsilyl, tetrahydropyranyl and tetrahydrofuranyl groups, and the like.

The vinylcopper complex (M is shown by the formula (IX)–(XII))of the formula (VI) is prepared against the α, β-unsaturated cyclopentenone in 1–10 equivalent, preferably 1–3 equivalent. Further, the reaction temperature of the conjugate addition reaction of the prepared vinylcopper complex and the α, β-unsaturated cyclopentenone is in the range between −100° C. and 0° C., preferably between −80° C. and −20° C. The reaction time varies by the reaction amount, the type of solvent used, and the reaction temperature, though it is from about 1 min. to 4 hours. The end point of the reaction is determined by the time when the α, β-unsaturated cyclopentenone disappears from the reaction system.

After the reaction, the uptake of an intermediate (VIII) of prostaglandins from the reaction mixture is carried out by quenching, extraction, liquid-separation, filtration and the like, followed by removal of organic solvent and then silica gel chromatography. An obtained intermediate of prostaglandins does not contain an geometrical isomer (13Z)-substance whose separation is extremely difficult, whereby the purification can easily be carried out.

By treating a prostaglandin intermediate shown by the formula (VIII) with acid, deprotection of the hydroxyl group of the 11 position is carried out to produce a prostaglandin shown by the formula (I)

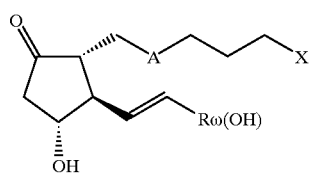

(I)

(wherein A, X and Rω(OH) have a same meaning as described before, and the stereochemistry of the formula (I) represents a relative steric configuration, and does not restricts an optically active form or a racemic form). The acids used here are an inorganic acid and an organic acid such as p-toluenesulfonic acid, preferably acetic acid, hydrofluoric acid or hydrochloric acid. The solvent used in the invention is water soluble and one which can solubilize a starting material (VIII), preferably acetonitrile, tetrahydrofuran or tetrahydrofuran containing water. The reaction temperature is in the range between −50° C. and 100° C., preferably between −20° C. and 60° C. The reaction time varies by the reaction amount, the type of reagent used, the type of solvent used and the reaction temperature, though it is usually from about 1 min. to 18 hours. The end point of the reaction is determined by the time when the compound (VIII) disappears from the reaction system.

After the reaction, the uptake of an prostaglandin (I) from the reaction mixture is carried out by extraction, liquid-separation, filtration and the like, followed by removal of organic solvent and then silica gel column chromatography.

The outline of the especially preferable preparation process of prostaglandins according to the invention is shown in the synthetic route (II) Without carrying out the protection of the hydroxyl group of the hydroxy-1-alkyne (XIII'), it is reacted with the tin hydride compound ($R^3$ has a same meaning as described before) shown by the formula (III) to give the (E,Z)-hyroxyvinylstannane compounds shown by the formula (IV'), followed by a silica gel column chromatographic separation to produce the (E)-hyroxyvinylstannane compound shown by the formula (V'). Under the condition that stochiometrically 1 equivalent of the copper (I) salt shown by CuY (Y has a same meaning as described before) and 3 equivalents of the alkyllithium reagent shown by $R^4Li$ ($R^4$ has a same meaning as described before) are added to the (E)-hyroxyvinylstannane compound, it is converted to the vinylcopper complex shown by the formula (IX'), whereby the α, β-unsaturated cyclopentenone ($R^1$ has a same meaning as described before) shown by the formula (VII') is added to produce the intermediate of prostaglandin ($R^1$ has a same meaning as described before) shown by the formula (VIII'). Further, the protecting group $R^1$ ($R^1$ has a same meaning as described before) of the compound is easily be deprotected by an appropriate acid to give prostaglandin shown by the formula (I'). A further detailed explanation of the reaction temperature, the reaction time, the used solvent and the like in a series of steps is same as described on the preparation process shown in the synthetic route (I).

Synthetic route (II)

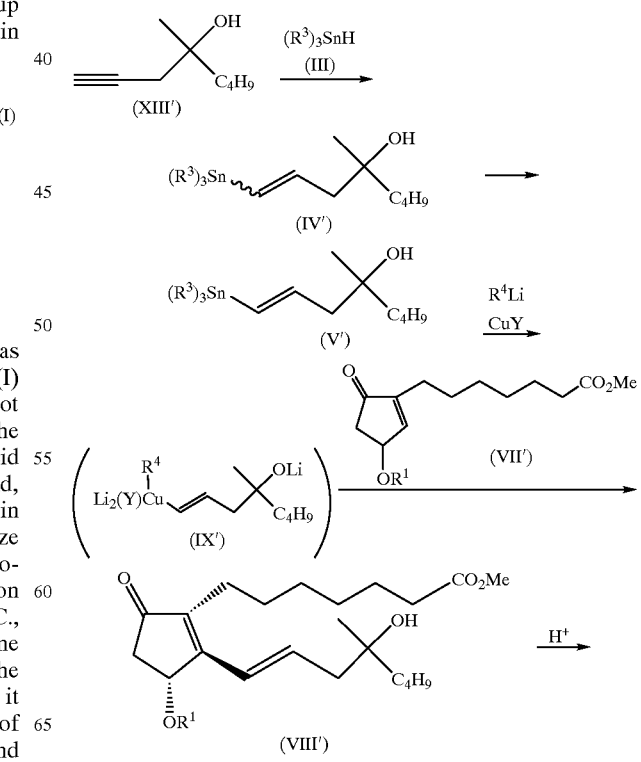

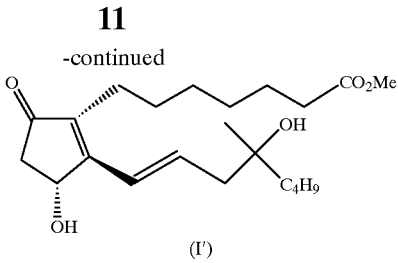

(I')

In the following, the invention will be explained in more detail by way of examples, but it is to be understood that the invention is not limited thereby in any way.

EXAMPLE 1

Preparation of [(4RS, 1E)-4-hydroxy-4-methyl-1-octynl] tri-n-butyltin

To 4-hydroxy-4-methyl-1-octyne (46.8 g, 0.33 mol), which was stirred and heated at 100° C. under nitrogen atmosphere, was dropped tri-n-butyltin hydride (126 g, 0.43 mol), and the mixture was stirred at 100–105° C. for 1 h. By analyzing the reaction mixture by HPLC it turned out that the E/Z ratio was 85:15. After confirming the disappearance of 4-hydroxy-4-methyl-1-octyne by TLC, the reaction mixture was cooled to room temperature, and purified by a medium pressure silica gel column chromatography [ethyl acetate/hexane (1/40)] to give 88.1 g (61% yield, the reaction conversion ratio was 96% by considering the obtained mixture of Z-substance and EZ-substance) of [(4RS, 1E)-4-hydroxy-4-methyl-1-octynl] tri-n-butyltin as a colorless oil;

IR (film): $v_{MAX}$=3370 cm$^{-1}$, 1600, 1460, 1375, 990. $^1$HNMR (90 MHz, CDCl$_3$): δ=0.72–1.09 (m, 18 H), 1.09–1.93 (m, 18 H), 1.16 (s, 3 H), 2.20–2.41 (m, 2 H), 5.91–6.11 (m, 2 H).

EXAMPLE 2

Preparation of (±)-methyl(16RS, 13E)-11-tert-butyldimethylsilyloxy-16-hydroxy-16-methyl-9-oxoprost-13-en-1-oate (process via a vinylcopper complex of the formula (IX) type)

Into a dry flask were placed copper (I) cyanide (188 mg, 2.1 mmol) and dry tetrahydrofuran (5 ml) under nitrogen atmosphere, and the mixture was cooled to 0° C. and was dropped with 6.7 ml (6.93 mmol) of a diethyl ether solution of methyllithium (1.03 mol/liter). After stirring at 0° C. for 30 min, a solution of [(4RS, 1E)-4-hydroxy-4-methyl-1-octenyl]tri-n-butyltin (1.03 g, 2.4 mmol) in dry tetrahydrofuran (3 ml) was dropped, and stirring was continued at the same temperature for 45 min. After cooling to –78° C., a solution of (±) methyl 7-(3-tert-butyldimethylsilyloxy-5-oxo1-cyclopentenyl)heptanoate (529 mg, 1.5 mmol) in dry tetrahydrofuran (2.5 ml) was rapidly added.

After stirring for 5 min, 70 ml of a saturated aqueous ammonium chloride/aqueous ammonia (9:1) was added, and stirring was continued for 30 min, letting the temperature rise gradually to room temperature. This mixture was extracted with ethyl acetate (100 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/5)] to give 622 mg (84% yield) of (±)-methyl(16RS, 13E)-11-tert-butyldimethylsilyloxy-16-hydroxy-16-methyl-9-oxoprost-13-en-1-oate as a colorless oil;

IR (film): $v_{MAX}$=3520 cm$^{-1}$, 1740, 1250, 975. $^1$H NMR (90 MHz, CDCl$_3$): δ=0.05 (s, 6 H), 0.73–1.10 (m, 12 H), 1.10–2.89 (m, 25 H), 1.17 (s, 3 H), 3.67 (s, 3 H), 4.04 (q, J=8.3 Hz, 1 H), 5.20–5.90 (m, 2 H).

EXAMPLE 3

Preparation of (±)-methyl(16RS, 13E)-11-tert-butyldimethylsilyloxy-16-hydroxy-16-methyl-9-oxoprost-13-en-1-oate (process via a vinylcopper complex of the formula (IX) type)

Into a dry flask were placed copper (I) cyanide (10.6 g, 118 mmol) and a solution of [(4RS, 1E)-4-hydroxy-4-methyl-1-octenyl]tri-n-butyltin (58.4 g, 135 mmol) in dry tetrahydrofuran (600 ml) under nitrogen atmosphere, and the mixture was cooled to 0° C. To this mixture was dropped 360 ml (389 mmol) of a diethyl ether solution of methyllithium (1.08 mol/liter), and stirring was continued for 1 h, letting the temperature rise gradually to room temperature. After cooling to –78° C., a solution of (±) methyl 7-(3-tert-butyldimethylsilyloxy-5-oxo-1-cyclopentenyl)heptanoate (30.0 g, 84.6 mmol) in dry tetrahydrofuran (140 ml) was rapidly added. After stirring for 5 min, 300 ml of a saturated aqueous ammonium chloride/aqueous ammonia (9:1) was added, and stirring was continued for 30 min, letting the temperature rise gradually to room temperature. This mixture was extracted with ethyl acetate (400 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/5)] to give 39.5 g (94% yield) of (±)-methyl(16RS, 13E)-11-tert-butyldimethylsilyloxy-16-hydroxy-16-methyl-9-oxoprost-13-en-1-oate as a colorless oil. The spectral data of IR and $^1$H NMR were identical with those of the example 2.

EXAMPLE 4

Preparation of (±)-methyl(16RS, 13E)-11-tert-butyldimethylsilyloxy-16-hydroxy-16-methyl-9-oxoprost-13-en-1-oate (process via a vinylcopper complex of the formula (IX) type)

Into a dry flask was placed a solution of [(4RS, 1E)-4-hydroxy-4-methyl-1-octenyl]tri-n-butyltin (1.36 g, 3.15 mmol) in dry tetrahydrofuran (5 ml) under nitrogen atmosphere, and the mixture was cooled to 0° C. To this solution was dropped 5.7 ml (5.99 mmol) of a diethyl ether solution of methyllithium (1.05 mol/liter), and stirring was continued for 1 h, letting the temperature rise gradually to room temperature. After cooling to –40° C., copper (I) cyanide (141 mg, 1.58 mmol) was added and dissolved by letting the temperature rise gradually to 0° C. This reaction liquid was cooled to –78° C. and added with a solution of (±) methyl 7-(3-tert-butyldimethylsilyloxy-5-oxo-1-cyclopentenyl)heptanoate (318 mg, 0.9 mmol) in dry tetrahydrofuran (1.5 ml) was rapidly added. After stirring for 5 min, 20 ml of a saturated aqueous ammonium chloride/aqueous ammonia (9:1) was added, and stirring was continued for 30 min, letting the temperature rise gradually to room temperature. This mixture was extracted with ethyl acetate (80 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/5)] to give 413 mg (96% yield) of (±)-methyl(16RS, 13E)-11-tertbutyldimethylsilyloxy-16-hydroxy-16-methyl-9-oxoprost-13-en-1-oate as a colorless oil. The spectral data of IR and $^1$H NMR were identical with those of the example 2.

EXAMPLE 5

Preparation of (−)-methyl(11R, 15S, 13E)-11-tert-butyldimethylsilyloxy-15-hydroxy-9-oxoprost-13-en1-oate (process via a vinylcopper complex of the formula (IX) type)

Into a dry flask was placed (S)-1-octyn-3-ol (2.00 g, 15.8 mmol) under nitrogen atmosphere, and azobisisobutyronitrile (25 mg, 0.15 mmol) and tri-n-butyltin hydride (5.11 ml, 19.0 mmol) were added and heated under stirring at 80° C. for 2 h. The reaction mixture was cooled to room temperature, and purified by a medium pressure silica gel column chromatography [ethyl acetate/hexane (1/5)] to give 4.80 g (73% yield) of [(3S, 1E)-3-hydroxy-1-octynl] tri-n-butyltin as a colorless oil. Into a dry flask were placed copper (I) cyanide (188 mg, 2.1 mmol) and dry tetrahydrofuran (5 ml) under nitrogen atmosphere, and the mixture was cooled to 0° C. and was dropped with 6.6 ml (6.75 mmol) of a diethyl ether solution of methyllithium (1.03 mol/liter). After stirring at 0° C. for 30 min, a solution of [(3S, 1E)-3-hydroxy-1-octenyl]tri-n-butyltin (939 mg, 2.25 mmol) in dry tetrahydrofuran (3 ml) was dropped at 0° C., and stirring was continued at room temperature for 30 min . The reaction liquid was cooled to −78° C. and added with a solution of (±) methyl 7-[(3R)-tert-butyldimethylsilyloxy-5-oxo-1-cyclopentenyl]heptanoate (529 mg, 1.5 mmol) in dry tetrahydrofuran (1.5 ml) was rapidly added. Stirring for 3 h to let the temperature rise gradually to −10° C., 30 ml of a saturated aqueous ammonium chloride/aqueous ammonia (9:1) was added, and stirring was continued for 30 min , letting the temperature rise gradually to room temperature. This mixture was extracted with ethyl acetate (100 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/6)] to give 448 mg (62% yield) of (−)-methyl(11R, 15S, 13E)-11-tert-butyldimethylsilyloxy-15-hydroxy-9-oxoprost-13-en-1-oate as a colorless oil;

IR (film): $v_{MAX}$=3470 cm$^{-1}$, 1740, 1250, 975. $^1$H NMR (90 MHz, CDCl$_3$): δ=0.04 (s, 6 H), 0.73–1.02 (m, 3 H), 0.88 (s, 9 H), 1.08–2.86 (m, 25 H), 3.65 (s, 3 H), 3.86–4.25 (m, 2 H), 5.49–5.70 (m, 2 H).

EXAMPLE 6

Preparation of (−)-methyl(11R, 15S, 5Z, 13E)-11-tert-butyldimethylsilyloxy-15-hydroxy-9-oxoprost-5,13-dien-1-oate (process via a vinylcopper complex of the formula (IX) type)

Into a dry flask were placed copper (I) cyanide (125 mg, 1.4 mmol) and a solution of [(3S, 1E)-3-hydroxy-1-octenyl]tri-n-butyltin (668 mg, 1.4 mmol) in dry tetrahydrofuran (3 ml) under nitrogen atmosphere, and the mixture was cooled to 0° C. To this mixture was dropped 4.4 ml (4.6 mmol) of a diethyl ether solution of methyllithium (1.05 mol/liter), and stirring was continued for 2 h, letting the temperature rise to room temperature. The reaction liquid was cooled to −78° C. and added with a solution of (±) methyl 7-[(3R)-tert-butyldimethylsilyloxy-5-oxo-1-cyclopentenyl]-4Z-heptenoate (350 mg, 1.0 mmol) in dry tetrahydrofuran (2 ml) was rapidly added. Stirring for 3 h, 20 ml of a saturated aqueous ammonium chloride/aqueous ammonia (9:1) was added, and stirring was continued for 30 min , letting the temperature rise gradually to room temperature. This mixture was extracted with ethyl acetate (100 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/6)] to give 278 mg (58% yield) of (−)-methyl(11R, 15S, 5Z, 13E)-11-tert-butyldimethylsilyloxy-15-hydroxy-9-oxoprost-5,13-dien-1-oate as a colorless oil;

IR (film): $v_{MAX}$=3470 cm$^{-1}$, 1740, 1245, 1150, 1110, 965, 770. $^1$H NMR (90 MHz, CDCl$_3$): δ=0.05 (s, 6 H), 0.73–1.02 (m, 3 H), 0.89 (s, 9 H), 1.08–2.89 (m, 20 H), 3.66 (s, 3 H), 3.85–4.24 (m, 2 H), 5.28–5.49 (m, 2 H), 5.52–5.72 (m, 2 H).

EXAMPLE 7

Preparation of (±)-methyl(16RS, 13E)-11-tert-butyldimethylsilyloxy-16-hydroxy-16-methyl-9-oxoprost-13-en-1-oate (process via a vinylcopper complex of the formula (X) type)

Into a dry flask was placed a solution of [(4RS, 1E)-4-hydroxy-4-methyl-1-octenyl]tri-n-butyltin (973 mg, 2.26 mmol) in dry tetrahydrofuran (5 ml) under nitrogen atmosphere and the mixture was cooled to 0° C. The solution was dropped with 5.1 ml (4.48 mmol) of a diethyl ether solution of methyllithium (0.88 mol/liter), warmed to room temperature and stirred for 2 h. After cooling to −40° C., copper (I) cyanide (200 mg, 2.26 mmol) was added and dissolved by letting the temperature rise gradually to 0° C. The reaction liquid was cooled to −78° C., dropped with boron trifluoride ether complex (283 µl, 2.26 mmol), stirred for 10 min and added with a solution of (±) methyl 7-(3-tert-butyldimethylsilyloxy-5-oxo-1-cyclopentenyl)heptanoate (500 mg, 1.4 mmol) in dry tetrahydrofuran (2 ml) was rapidly added. After stirring for 30 min , 20 ml of a saturated aqueous ammonium chloride/aqueous ammonia (9:1) was added, and stirring was continued for 20 min, letting the temperature rise gradually to room temperature. This mixture was extracted with ethyl acetate (70 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/5)] to give 522 mg (75% yield) of (±)-methyl(16RS, 13E)-11-tert-butyldimethylsilyloxy-16-hydroxy-16-methyl-9-oxoprost-13-en-1-oate as a colorless oil. The spectral data of IR and $^1$H NMR were identical with those of the example 2.

EXAMPLE 8

Preparation of (−)-methyl(11R, 15S, 13E)-11-tert-butyldimethylsilyloxy-15-hydroxy-9-oxoprost-13-en-1-oate (process via a vinylcopper complex of the formula (X) type)

A solution of [(3S, 1E)-3-hydroxy-1-octenyl]tri-n-butyltin (668 mg, 1.6 mmol) in dry tetrahydrofuran (5 ml) was placed into a dry flask under nitrogen atmosphere and cooled to 0° C. The solution was dropped with 3.1 ml (3.2 mmol) of a diethyl ether solution of methyllithium (1.05 mol/liter), warmed to room temperature and stirred for 2 h. After cooling to −40° C., copper (I) cyanide (125 mg, 1.4 mmol) was added and dissolved by letting the temperature rise gradually to 0° C. The reaction liquid was cooled to −78° C., dropped with boron trifluoride ether complex (160 μl, 1.3 mmol), stirred for 10 min and added with a solution of (±)-methyl 7-[(3R)-tert-butyldimethylsilyloxy-5-oxo-1-cyclopentenyl)heptanoate (352 mg, 1.0 mmol) in dry tetrahydrofuran (2 ml) was rapidly added. After stirring for 40 min, 20 ml of a saturated aqueous ammonium chloride/aqueous ammonia (9:1) was added, and stirring was continued for 20 min, letting the temperature rise gradually to room temperature. This mixture was extracted with ethyl acetate (70 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/6)] to give 340 mg (71% yield) of (−)-methyl(11R, 15S, 13E)-11-tert-butyldimethylsilyloxy-15-hydroxy-9-oxoprost-13-en-1-oate as a colorless oil. The spectral data of IR and $^1$H NMR were identical with those of the example 5.

EXAMPLE 9

Preparation of (−)-methyl(11R, 15S, 13E)-11-tert-butyldimethylsilyloxy-15-hydroxy-9-oxoprost-13-en-1-oate (process via a vinylcopper complex of the formula (XI) type)

Into a dry flask were placed copper (I) cyanide (125 mg, 1.4 mmol) and a solution of [(3S, 1E)-3-hydroxy-1-octenyl]tri-n-butyltin (668 mg, 1.6 mmol) in dry tetrahydrofuran (5 ml) under nitrogen atmosphere, and the mixture was cooled to 0° C. To this mixture was dropped 4.4 ml (4.6 mmol) of a diethyl ether solution of methyllithium (1.05 mol/liter), and stirring was continued for 2 h, letting the temperature rise to room temperature. The reaction liquid was cooled to −78° C., dropped with boron trifluoride ether complex (160 μl, 1.3 mmol), stirred for 10 min and added with a solution of (±)-methyl 7-[(3R)-tert-butyldimethylsilyloxy-5-oxo-1-cyclopentenyl)heptanoate (352 mg, 1.0 mmol) in dry tetrahydrofuran (2 ml) was rapidly added. After stirring for 40 min, 20 ml of a saturated aqueous ammonium chloride/aqueous ammonia (9:1) was added, and stirring was continued for 20 min, letting the temperature rise gradually to room temperature. This mixture was extracted with ethyl acetate (70 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/6)] to give 349 mg (73% yield) of (−)-methyl(11R, 15S, 13E)-11-tert-butyldimethylsilyloxy-15-hydroxy-9-oxoprost-13-en-1-oate as a colorless oil. The spectral data of IR and $^1$H NMR were identical with those of the example 5.

EXAMPLE 10

Preparation of (±)-methyl(16RS, 13E)-11-tert-butyldimethylsilyloxy- 16-hydroxy-16-methyl-9-oxoprost-13-en-1-oate (process via a vinylcopper complex of the formula (XII) type)

Into a dry flask was placed a solution of [(4RS, 1E)-4-hydroxy-4-methyl-1-octenyl]tri-n-butyltin (973 mg, 2.26 mmol) in dry tetrahydrofuran (5 ml) under nitrogen atmosphere and the mixture was cooled to 0° C. The solution was dropped with 5.7 ml (4.97 mmol) of a diethyl ether solution of methyllithium (0.88 mol/liter), warmed to room temperature and stirred for 2 h. After cooling to −78° C., the mixture was added with a previously prepared solution of copper (I) cyanide (215 mg, 2.4 mmol) and lithium chloride (102 mg, 2.4 mmol) in dry tetrahydofuran (3 ml) by using a cannula, and stirred for 1 h. The reaction liquid was dropped with boron trifluoride ether complex (283 μl, 2.26 mmol), stirred for 10 min and added with a solution of (±) methyl 7-(3-tert-butyldimethylsilyloxy-5-oxo-1-cyclopentenyl) heptanoate (500 mg, 1.4 mmol) in dry tetrahydrofuran (2 ml) was rapidly added. After stirring for 30 min, 20 ml of a saturated aqueous ammonium chloride/aqueous ammonia (9:1) was added, and stirring was continued for 20 min, letting the temperature rise gradually to room temperature. This mixture was extracted with ethyl acetate (70 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/5)] to give 590 mg (85% yield) of (±)-methyl(16RS, 13E)-11-tert-butyldimethylsilyloxy-16-hydroxy-16-methyl-9-oxoprost-13-en-1-oate as a colorless oil. The spectral data of IR and $^1$H NMR were identical with those of the example 2.

EXAMPLE 11

Preparation of (−)-methyl(11R, 15S, 5Z, 13E)-11-tert-butyldimethylsilyloxy-15-hydroxy-9-oxoprost-5, 13-dien-1-oate (process via a vinylcopper complex of the formula (XII) type)

A solution of [(3S, 1E)-3-hydroxy-1-octenyl]tri-n-butyltin (668 mg, 1.6 mmol) in dry tetrahydrofuran (5 ml) was placed into a dry flask under nitrogen atmosphere and cooled to 0° C. The solution was dropped with 3.1 ml (3.2 mmol) of a diethyl ether solution of methyllithium (1.05 mol/liter), warmed to room temperature and stirred for 2 h. After cooling to −78° C., the mixture was added with a previously prepared solution of copper (I) cyanide (125 mg, 1.4 mmol) and lithium chloride (59 mg, 1.6 mmol) in dry tetrahydofuran (3 ml) by using a cannula, and stirred for 1 h. The reaction liquid was dropped with boron trifluoride ether complex (160 μl, 1.3 mmol), stirred for 10 min and added with a solution of (±) methyl 7-[(3R)-tert-butyldimethylsilyloxy-5-oxo-1-cyclopentenyl)-4Z-heptenoate (350 mg, 1.0 mmol) in dry tetrahydrofuran (2 ml) was rapidly added. After stirring for 1.5 h, 20 ml of a saturated aqueous ammonium chloride/aqueous ammonia (9:1) was added, and stirring was continued for 20 min, letting the temperature rise gradually to room temperature. This mixture was extracted with ethyl acetate (70 ml) two times, and the combined organic layer was washed with a saturated aqueous sodium chloride, dried over anhydrous magnesium sulfate, and concentrated in vacuo to remove solvent. The residue was purified by silica gel column chromatography [ethyl acetate/hexane (1/6)] to give 330 mg (69% yield) of (−)-methyl(11R, 15S, 5Z, 13E)-11-tert-butyldimethylsilyloxy-15-hydroxy-9-oxoprost-5,13-dien1-oate as a colorless oil. The spectral data of IR and $^1$H NMR were identical with those of the example 6.

EXAMPLE 12

Preparation of (±)-methyl(16RS, 13E)-11, 16-dihydroxy-16-methyl-9-oxoprost-13-en-1-oate (Misoprostol)

Into a Teflon container were placed (±)-methyl(16RS, 13E)-11-tert-butyldimethylsilyloxy-16-hydroxy-16-methyl-9-oxoprost-13-en-1-oate (1.89 g, 3.81 mmol) and acetonitrile (50 ml), whereby 46% hydrofluoric acid (4.5 ml) was added and stirred at room temperature for 2 h. The reaction mixture was added with water (120 ml) and extracted with methylene chloride (60 ml) two times. The combined organic layer was washed with a saturated aqueous sodium hydrogencarbonate, a saturated aqueous sodium chloride, dried over anhydrous magnesium sulfate, and concentrated in vacuo to remove solvent. The residue was purified by silica gel column chromatography [ethyl acetate/hexane (2/1)] to give 1.44 g (99% yield) of Misoprostol;

IR (film): $v_{MAX}$=3400 cm$^{-1}$, 1720, 1710, 1160, 970. $^1$HNMR (90 MHz, CDCl$_3$): δ=0.92 (t, J=7 Hz, 3 H), 1.10–1.80 (m, 16 H), 1.17 (s, 3 H), 1.80–2.90 (m, 8 H), 3.66 (s, 3 H), 4.03 (q, J=9 Hz, 1 H), 5.38 (dd, J=15, 9 Hz, 1 H), 5.68 (dt, J=15, 7 Hz, 1 H).

EXAMPLE 13

Preparation of (–)-methyl(11R, 15S, 13E)-11, 15-dihydroxy-9-oxoprost-13-en1-oate (prostaglandin E$_1$ methyl ester)

(–)-methyl(11R, 15S, 13E)-11-tert-butyldimethylsilyloxy-15-hydroxy-9-oxoprost-13-en-1-oate (481 mg, 1.0 mmol) was dissolved in 5 ml of a mixed solvent (ethyl acetate/water/tetrahydrofuran 6:3:1) and stirred at 40° C. for 2 h. The reaction mixture was poured into a saturated aqueous sodium carbonate cooled with ice and extracted with ethyl acetate (100 ml) two times. The combined organic layer was washed with a saturated aqueous sodium chloride, dried over anhydrous magnesium sulfate, and concentrated in vacuo to remove solvent. The residue was purified by silica gel column chromatography [ethyl acetate/hexane (2/1)] to give 312 mg (85% yield) of prostaglandin E$_1$ methyl ester;

IR (film): $v_{MAX}$=3380 cm$^{-1}$, 1735, 965. $^1$H NMR (90 MHz, CDCl$_3$): δ=0.87 (br. t, 3 H), 1.04–2.92 (m, 24 H), 3.64 (s, 3 H), 3.76–4.20 (m, 2 H), 5.40–5.70 (m, 2 H).

EXAMPLE 14

Preparation of (–)-methyl(11R, 15S, 5Z, 13E)-11, 15-dihydroxy-9-oxoprost-5,13-dien1-oate (prostaglandin E$_2$ methyl ester)

(–)-methyl(11R, 15S, 5Z, 13E)-11-tert-butyldimethylsilyloxy-15-hydroxy-9-oxoprost-5,13-dien1-oate (518 mg, 1.08 mmol) and acetonitrile (10 ml) were placed into a Teflon container and cooled to 0° C., whereby 46% hydrofluoric acid (1.0 ml) was added and stirred for 2 h. The reaction mixture was poured into a saturated aqueous sodium carbonate cooled with ice and extracted with ethyl acetate (150 ml) two times. The combined organic layer was washed with a saturated aqueous sodium chloride, dried over anhydrous magnesium sulfate, and concentrated in vacuo to remove solvent. The residue was purified by silica gel column chromatography [ethyl acetate/hexane (2/1)] to give 345 mg (88% yield) of prostaglandin E$_2$ methyl ester;

IR (film): $v_{MAX}$=3380 cm$^{-1}$, 1735, 1150, 1070, 965. $^1$H NMR (90 MHz, CDCl$_3$): δ=0.70–1.06 (br. t,3 H), 1.06–1.87 (m, 10 H), 1.86–2.92 (m, 10 H), 3.20–3.59 (m, 1 H), 3.65 (s, 3 H), 3.81–4.55 (m, 5 H), 5.20–5.80 (m, 4 H).

What is claimed is:
1. Process for preparing prostaglandins shown by the formula (I)

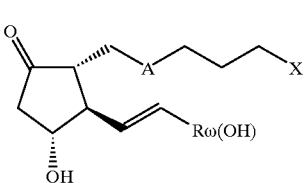

(wherein A is ethylene or (Z)-vinylene, X is CH$_2$OR$^2$ or CO$_2$R$^2$, R$^2$ is an alkyl group of the carbon number of 1–5, H or a protecting group, Rω(OH) is a straight chain or branch chain alkyl group of the carbon number of 4–10 having a secondary or tertiary hydroxyl group, the steric configuration of hydroxyl group is R, S or a mixture of R and S, the steric configuration of branched chain alkyl group is R, S or a mixture of R and S, the stereochemistry of the formula (I) represents a relative steric configuration, and does not restrict an optically active substance or a racemic substance), comprising the steps, wherein
  (a) a hydroxy-1-alkyne shown by the formula (II)

Rω(OH) has a same meaning as described above) is reacted with a tin hydride shown by the formula (III)

(wherein R$^3$ is a lower alkyl group of the carbon number of 1–6, phenyl or cyclohexyl) to prepare subsequently (E,Z)-hydroxyvinylstannanes shown by the formula (IV)

(wherein R$^3$ and Rω(OH) have a same meaning as described above),
  (b) the (E)-substance and the (Z)-substance of (E, Z)-hydroxyvinylstannane compound are separated to prepare an (E)-hydroxyvinylstannane shown by the formula (V)

(wherein R$^3$ and Rω(OH) have a same meaning as described above),
  (c) a copper (I) salt shown by CuY (Y is —CN, —SCN or —OSO$_2$CF$_3$) and an alkyllithium reagent shown by R$^4$Li (R$^4$ is a lower alkyl) are added, or
    CuY (Y has a same meaning as described before), R$^4$Li (R$^4$ has a same meaning as described before) and Lewis acid are added, or
    CuY (Y has a same meaning as described before), R$^4$Li (R$^4$ has a same meaning as described before), Lewis acid and a lithium salt shown by LiZ (Z is a halogen atom or —OSO$_2$CF$_3$) are added, to give a vinylcopper complex shown by the formula (VI)

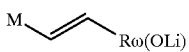
(VI)

(wherein M is a reactive copper part having Y and Li, or a reactive copper part having Y, Li and Lewis acid, or a reactive copper part having Y, Li, Lewis acid and LiZ, Rω(OLi) represents a group in which hydrogen of the hydroxyl group in Rω(OH) is exchanged by Li), (d) a conjugate addition to an α, β-unsaturated cyclopentenone of the formula (VII)

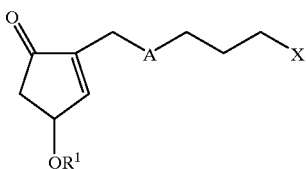
(VII)

(wherein $R^1$ is a protecting group, A and X have a same meaning as described before, and the formula (VII) does not restrict an optically active form or a racemic form) is carried out to prepare an intermediate of prostaglandins shown by the formula (VIII)

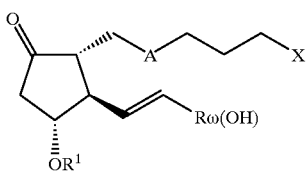
(VIII)

(wherein $R^1$, A, X and Rω(OH) have a same meaning as described before, and the stereochemistry of the formula (VIII) represents a relative steric configuration, and does not restrict an optically active form or a racemic form), and (e) the intermediate of prostaglandins shown by the formula (VIII) is treated with acid to carry out, the deprotection reaction.

2. Process according to claims 1, wherein the hydroxy-1-alkyne (II) is a 4-hydroxy-4-alkyl-1-alkyne shown by the formula (XIII)

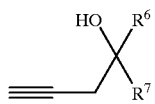
(XIII)

(wherein $R^6$ and $R^7$ are each independently a straight chain or branched chain alkyl group of the carbon number of 1–7 or hydrogen, and the steric configuration of the hydroxy group is R, S or a mixture of R and S).

3. Process according to claims 1, wherein the hydroxy-1-alkyne (II) is a 3-hydroxy-1-alkyne shown by the formula (XIV)

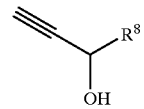
(XIV)

(wherein $R^8$ represents a straight chain or branched chain alkyl group of the carbon number of 3–9, and the steric configuration of the hydroxy group is R, S or a mixture of R and S).

4. Process according to claim 1, wherein in the formula (VI) M is a vinylcopper complex shown by the formula (IX)

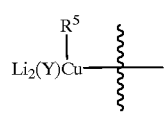
(IX)

(wherein $R^5$ represents $R^4$ or

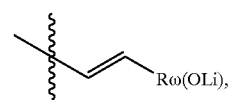

and $R^4$, Y and Rω(OLi) have a same meaning as described before).

5. Process according to claim 1, wherein in the formula (VI) M is a vinylcopper complex shown by the formula (X)

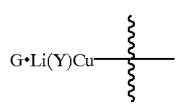
(X)

(wherein G represents Lewis acid, and Y has a same meaning as described before).

6. Process according to claim 1, wherein in the formula (VI) M is a vinylcopper complex shown by the formula (XI)

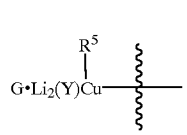
(XI)

(wherein $R^5$ represents $R^4$ or

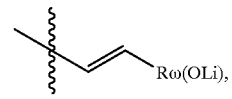

and $R^4$, Y and Rω(OLi) have a same meaning as described before).

7. Process according to claim 1, wherein in the formula (VI) M is a vinylcopper complex shown by the formula (XII)

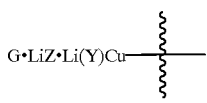 (XII)

(wherein Z, G and Y have a same meaning as described before).

8. The process according to claim 1, wherein step (b) further comprises conducting said separation by chromatography.

9. Process for preparing prostaglandins shown by the formula (I)

(wherein A, X, and Rω(OH) have the same meaning as described in claim 1, and the stereochemistry of formula (I) represents a relative steric configuration, and does not restrict an optically active form or a racemic form) comprising, treating an intermediate of prostroglandins shown by the formula (VIII) with acid.

* * * * *